(12) United States Patent
Hu et al.

(10) Patent No.: US 8,728,439 B2
(45) Date of Patent: May 20, 2014

(54) SYSTEM AND METHOD FOR INDIRECTLY MEASURING CALCIUM ION EFFLUX

(75) Inventors: Tom Chih-Chuang Hu, Rockville, MD (US); Benjamin J. Waghorn, Augusta, GA (US)

(73) Assignee: Celtrast LLC, Augusta, GA (US)

( * ) Notice: Subject to any disclaimer, the term of this patent is extended or adjusted under 35 U.S.C. 154(b) by 407 days.

(21) Appl. No.: 12/412,966

(22) Filed: Mar. 27, 2009

(65) Prior Publication Data

US 2009/0246144 A1 Oct. 1, 2009

Related U.S. Application Data

(60) Provisional application No. 61/072,263, filed on Mar. 31, 2008.

(51) Int. Cl.
*A61B 5/055* (2006.01)

(52) U.S. Cl.
USPC ............. 424/9.3; 424/9.36; 424/9.1; 382/133

(58) Field of Classification Search
None
See application file for complete search history.

(56) References Cited

U.S. PATENT DOCUMENTS

| | | | |
|---|---|---|---|
| 6,846,641 | B2 | 1/2005 | Wieloch et al. |
| 2002/0090341 | A1 | 7/2002 | Watson et al. |
| 2004/0096520 | A1 | 5/2004 | Nonotte et al. |
| 2004/0242994 | A1 | 12/2004 | Brady et al. |
| 2005/0136002 | A1 | 6/2005 | Fossheim et al. |
| 2005/0249667 | A1 | 11/2005 | Tuszynski et al. |
| 2006/0235292 | A1 | 10/2006 | Rongved et al. |
| 2007/0293436 | A1 | 12/2007 | Peterson et al. |
| 2008/0044827 | A1 | 2/2008 | Bogdanov et al. |
| 2008/0081021 | A1 | 4/2008 | Bilgen et al. |
| 2010/0166667 | A1 | 7/2010 | Jynge et al. |

FOREIGN PATENT DOCUMENTS

| | | |
|---|---|---|
| WO | 2007122553 | 11/2007 |
| WO | 2008093999 | 8/2008 |
| WO | 2010093635 | 8/2010 |

OTHER PUBLICATIONS

Saeed et al. Eur. Radiol. 10, 310-318.*
Rowland and Tozer. Clinical Pharmacokinetics pp. 18-31.*
Medina et al. Contrast Media Mol. Imaging 2007. 2: 248-257.*
Tanaka et al. Br. J. Pharmacol. 2002. 135, 1096-1100.*
Hu et al. NMR Biomed. 2004, 17, 620-626.*
Written Opinion and International Search Report of the International Searching Authority for PCT Application Serial No. PCT/US2009/038577, Jun. 16, 2009, pp. 1-9.
Dhalla NS, Pierce GN, Panagia V, Singal PK, Beamish RE. Calcium movements in relation to heart function. Basic Res Cardiol 1982; 77; 2: 117-139.
Caroni P, Carafoli E. An ATP-dependent Ca2+-pumping system in dog heart sarcolemma. Nature 1980; 283; 5749: 765-767.
Bassani JW, Bassani RA, Bers DM. Relaxation in rabbit and rat cardiac cells: species-dependent differences in cellular mechanisms. J Physiol 1994; 476; 2: 279-293.
Varro A, Negretti N, Hester SB, Eisner DA. An estimate of the calcium content of the sarcoplasmic reticulum in rat ventricular myocytes. Pflugers Arch 1993; 423; 1-2: 158-160.
Antoons G, Mubagwa K, Nevelsteen I, Sipido KR. Mechanisms underlying the frequency dependence of contraction and [Ca2+]i transients in mouse ventricular myocytes. J Physiol 2002; 543; Pt 3: 889-898.
Houser SR, Piacentino V, 3rd, Weisser J. Abnormalities of calcium cycling in the hypertrophied and failing heart. J Mol Cell Cardiol 2000; 32; 9: 1595-1607.
Saini HK, Shao Q, Musat S, Takeda N, Tappia PS, Dhalla NS. Imidapril treatment improves the attenuated inotropic and intracellular calcium responses to ATP in heart failure due to myocardial infarction. Br J Pharmacol 2005; 144; 2: 202-211.
Zhang XQ, Musch TI, Zelis R, Cheung JY. Effects of impaired Ca2+ homeostasis on contraction in postinfarction myocytes. J Appl Physiol 1999; 86; 3: 943-950.
Mendonca-Dias MH, Gaggelli E, Lauterbur PC. Paramagnetic contrast agents in nuclear magnetic resonance medical imaging. Semin Nucl Med 1983; 13; 4: 364-376.
Cory DA, Schwartzentruber DJ, Mock BH. Ingested manganese chloride as a contrast agent for magnetic resonance imaging. Magn Reson Imaging 1987; 5; 65-70.
Anderson M. Mn ions pass through calcium channels. A possible explanation. J Gen Physiol 1983; 81; 6: 805-827.
Narita K, Kawasaki F, Kita H. Mn and Mg influxes through Ca channels of motor nerve terminals are prevented by verapamil in frogs. Brain Res 1990; 510; 2: 289-295.
Shibuya I, Douglas WW. Indications from Mn-quenching of Fura-2 fluorescence in melanotrophs that dopamine and baclofen close Ca channels that are spontaneously open but not those opened by high [K+]O; and that Cd preferentially blocks the latter. Cell Calcium 1993; 14; 1: 33-44.
Hu TC, Pautler RG, MacGowan GA, Koretsky AP. Manganese-enhanced MRI of mouse heart during changes in inotropy. Magn Reson Med 2001; 46; 5: 884-890.
Skjold A, Kristoffersen A, Vangberg TR, Haraldseth O, Jynge P, Larsson HB. An apparent unidirectional influx constant for manganese as a measure of myocardial calcium channel activity. J Magn Reson Imaging 2006; 24; 5: 1047-1055.
Takahashi K, Takahashi T, Suzuki T, Onishi M, Tanaka Y, Hamano-Takahashi A, Ota T, Kameo K, Matsuda T, Baba A. Protective effects of SEA0400, a novel and selective inhibitor of the Na+/Ca2+ exchanger, on myocardial ischemia-reperfusion injuries. Eur J Pharmacol 2003; 458; 1-2: 155-162.
Tani M, Neely JR. Role of intracellular Na+ in Ca2+ overload and depressed recovery of ventricular function of reperfused ischemic rat hearts. Possible involvement of H+-Na+ and Na+-Ca2+exchange. Circ. Res. 1989; 65(4): 1045-1056.

(Continued)

Primary Examiner — Michael G Hartley
Assistant Examiner — Sean R Donohue
(74) Attorney, Agent, or Firm — Gardner, Groff, Greenwald & Villanueva, P.C.

(57) ABSTRACT

A system and method for indirectly measuring calcium ion efflux from a cell of a subject by using manganese ions as a surrogate marker for calcium is disclosed. Manganese ion efflux is measured with a MEMRI $T_1$-mapping method while the calcium-sodium exchanger is inhibited.

21 Claims, 5 Drawing Sheets

(56) References Cited

OTHER PUBLICATIONS

Kusuoka H, Camilion de Hurtado MC, Marban E. Role of sodium/calcium exchange in the mechanism of myocardial stunning: protective effect of reperfusion with high sodium solution. J. Am. Coll. Cardiol. 1993; 21(1): 240-248.

Yoshiyama M., Nakamura Y, Omura T, Hayashi T., Takagi Y, Hasegawa T., Nishioka H, Takeuchi K, Iwao H., Youshikawa J. Cardioprotective effect of SEA0400, a selective inhibitor of the Na+/Ca2+ exchanger, on myocardial ischemia-reperfusion injury in rats. J. Pharmacol. Sci. 2004; 95(2): 196-202.

Matsuda T, Arakawa N, Takuma K, Kishida Y, Kawasaki Y, Sakaue M, Takahashi K, Takahashi T, Suzuki T., Ota T, Hamano-Takahashi A, Onishi M, Tanaka Y, Kameo K, Baba A. SEA0400, a novel and selective inhibitor of the Na+-Ca2+ exchanger, attenuates reperfusion injury in the in vitro and in vivo cerbral ischemic models. J. Pharmacol. Exp. There. 2001; 298(1): 249-256.

Hu TC, Christian TF, Aletras AH, Taylor JL, Koretsky AP, Arai AE. Manganese enhanced magnetic resonance imaging of normal and ischemic canine heart. Magn Reson Med 2005; 54; 1: 196-200.

Frahm J, Haase A, Matthaei D. Rapid NMR imaging of dynamic processes using the FLASH technique. Magn Reson Med 1986; 3; 2: 321-327.

Chuang KH, Koretsky A. Improved neuronal tract tracing using manganese enhanced magnetic resonance imaging with fast T1 mapping. Magn Reson Med 2006; 55; 3: 604-611.

Loening AM, Gambhir SS. Amide: A free software tool for multimodality medical image analysis. Mol Imaging 2003; 2; 3: 131-137.

Webb Al, Weaver BM. The density of equine tissue at 37 degrees C. Res Vet Sci 1979; 26; 1: 71-75.

Nordhoy W, Anthonsen HW, Bruvold M, Brurok H, Skarra S, Krane J, Jynge P. Intracellular manganese ions provide strong T1 relaxation in rat myocardium. Magn Reson Med 2004; 52; 3: 506-514.

Lee C, Visen NS, Dhalla NS, Le HD, Isaac M, Choptiany P, Gross G, Omelchenko A, Matsuda T, Baba A, Takahashi K, Hnatowich M, Hryshko LV. Inhibitory profile of SEA0400 [2-[4-[(2,5-difluorophenyl)methoxy]phenoxy]-5-ethoxyaniline] assessed on the cardiac Na+-Ca2+ exchanger, NCX1.1. J Pharmacol Exp Ther 2004; 311; 2: 748-757.

Farkas AS, Acsai K, Nagy N, Toth A, Fulop F, Seprenyi G, Birinyi P, Nanasi PP, Forster T, Csanady M, Papp JG, Varro A, Farkas A. Na+/Ca2+ exchanger inhibition exerts a positive inotropic effect in the rat heart, but fails to influence the contractility of the rabbit heart. Br J Pharmacol 2008; 154; 1: 93-104.

International Search Report dated Aug. 30, 2010 for international application No. PCT/US2010/023641.

US Office Action for U.S. Appl. No. 13/145,036 dated Mar. 22, 2013.

* cited by examiner

SYSTEM AND METHOD FOR INDIRECTLY MEASURING CALCIUM ION EFFLUX

CROSS REFERENCE TO RELATED APPLICATION

This application claims priority to U.S. provisional application Ser. No. 61/072,263 filed Mar. 31, 2008, which is hereby incorporated by reference in its entirety for all of its teachings.

FIELD OF THE INVENTION

The present invention is directed generally to a system and method for indirectly measuring calcium ion efflux from a cell using manganese containing compounds and imaging techniques.

BACKGROUND OF THE INVENTION

Calcium ($Ca^{2+}$) is a major regulator of cardiac contractility. When a myocyte is depolarized by an action potential, $Ca^{2+}$ enters the cell primarily via L-type voltage-gated $Ca^{2+}$ channels with a smaller contribution occurring via the reverse mode of the sodium-calcium exchanger (NCX) channels. This $Ca^{2+}$ influx in the cytosol acts to trigger a subsequent release of $Ca^{2+}$ stored in the sarcoplasmic reticulum through $Ca^{2+}$-release channels ultimately leading to myocardial contraction The efflux of $Ca^{2+}$ occurs via the forward mode of the NCX and via the plasma membrane $Ca^{2+}$-ATPase mechanism. The net $Ca^{2+}$ flux through the NCX occurs in the outward direction. Previous studies estimating the relative contributions to $Ca^{2+}$ efflux have shown that the NCX is the dominant mechanism with 9-32% of the efflux occurring from non-NCX mechanisms in rats and 19% in mice.

Alterations in myocyte $Ca^{2+}$ handling are prevalent in the dysfunctional characteristics of a failing heart. Moreover, the NCX inhibitor SEA0400 has been shown to therapeutically reduce myocardial injury due to abnormal intracellular $Ca^{2+}$ handling. While this inhibitor is useful in treating abnormal intracellular $Ca^{2+}$ handling, it would be useful to monitor $Ca^{2+}$ influx and efflux in vivo; however, no techniques exist to either directly or indirectly observe in vivo intracellular $Ca^{2+}$ fluctuations across the plasma membrane.

SUMMARY OF THE INVENTION

Described herein are methods for indirectly measuring calcium ion efflux from a cell or a subject. The methods involve measuring the amount of manganese ion efflux from a cell or in a subject using imaging techniques. Once the manganese ion efflux concentration has been measured, the calcium ion efflux concentration can be correlated based on the ion efflux concentration. By accurately measuring calcium ion efflux concentration, it is possible to select and administer therapeutic agents to a subject experiencing increased calcium ion reflux.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, compounds, compositions, methods, conditions, or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a cell" includes two or more cells, and the like.

"Optional" or "optionally" means that the subsequently described event or circumstance can or cannot occur, and that the description includes instances where the event or circumstance occurs and instances where it does not.

Figure 1:
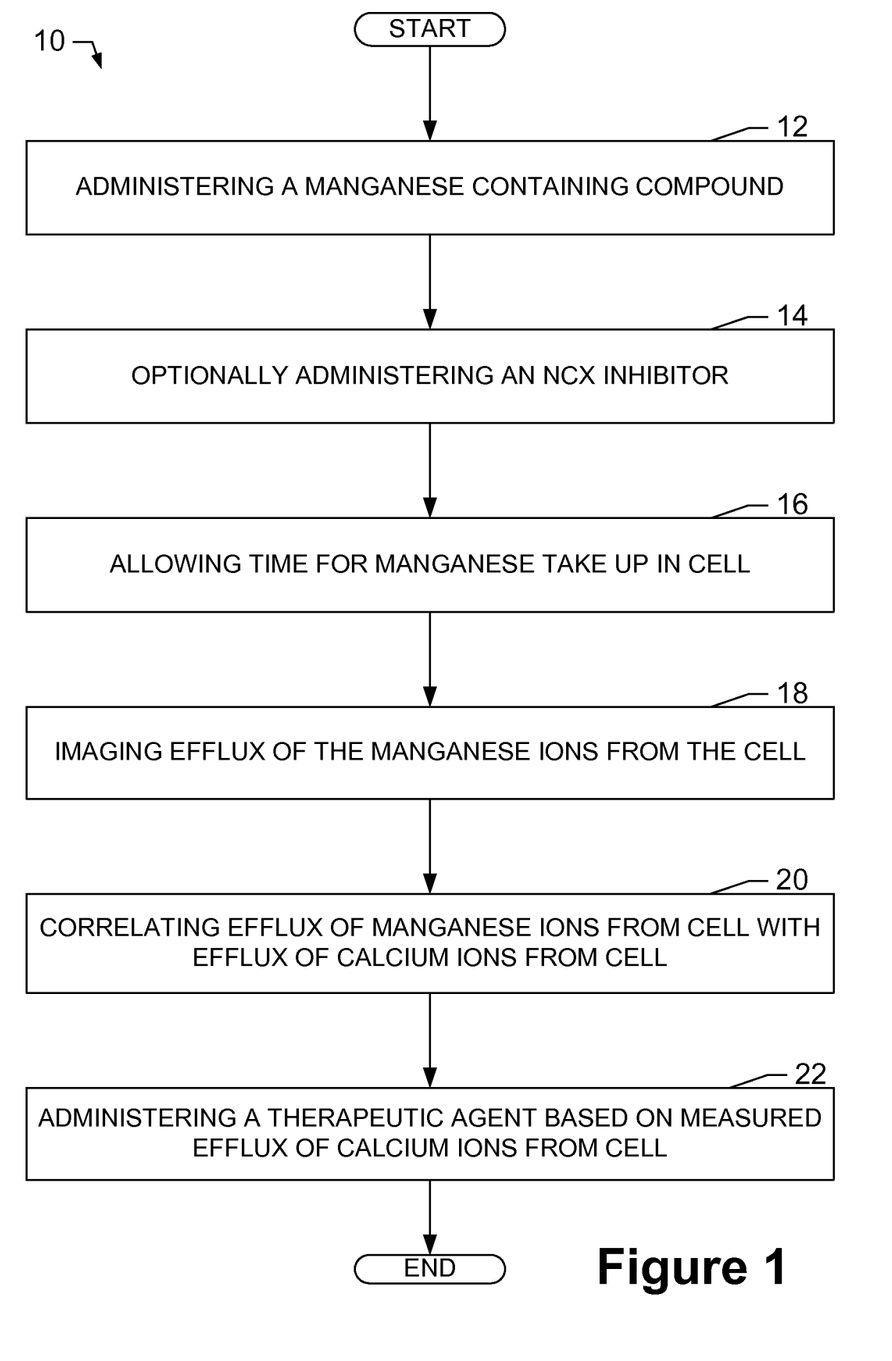
FIG. 1 is a flow diagram of a method of indirectly measuring calcium efflux from a cell according to an example embodiment of the present invention.

Referring now to FIG. 1, the present invention provides a method 10 for indirectly measuring calcium efflux from a cell of a human or animal subject by using magnesium ions as a surrogate marker or molecular contrast agent. The term "indirectly" as defined herein refers to the use of the methods described herein to measure calcium efflux from a cell without directly measuring the calcium concentration. As will be described below in greater detail, a manganese containing compound can be used to qualitatively and quantitatively predict calcium efflux from a cell. A manganese ion ($Mn^{2+}$) has a comparable ionic radius and comparable chemical properties to that of a calcium ion ($Ca^{2+}$). Additionally, manganese ions shorten the proton magnetization $T_1$ relaxation time during manganese-enhanced magnetic resonance imaging (MEMRI). Furthermore, $Mn^{2+}$ enters viable myocardial tissue via the L-type voltage-gated $Ca^{2+}$ channels and accumulates in the excitable myocardial cells in an additive fashion. Without wishing to be bound by theory, it is theorized that the ability to measure $Mn^{2+}$ efflux in vivo using MEMRI as a quantitative imaging approach reflects actual myocardial $Ca^{2+}$ efflux.

Calcium ion effluxes within a cell or subject are often associated with abnormal cellular events which may lead to cellular damage within cell culture or a subject and to tissue damage in a subject. Depending on the abnormal cellular event, apoptosis may occur or in the alternative cellular and tissue necrosis may occur. An abnormal cellular event includes, for example, an ischemic event such as heart palpitations, a myocardial infarction, chest pain, shortness of breath, nausea, vomiting, sweating, anxiety, fatigue, atrial fibrillation, heart attack, cardiac arrest, heart failure, or any combination thereof.

Without wishing to be bound by theory, it is theorized that if the cells or tissues undergoing an ischemic event are assayed using the system and methods described herein shortly after the onset of an ischemic event, the magnitude of cellular damage and tissue damage may be reversed by the quick administration of appropriate therapeutic agents. Alternatively, if cellular damage and tissue damage cannot be reversed, the magnitude of cellular and tissue damage may be predicted and quantified.

The method 10 for indirectly measuring calcium efflux from a cell of a human or animal subject begins at step 12 when a practitioner administers a manganese containing compound or manganese ions to the human or animal subject orally, intravenously, subcutaneously, intramuscularly, or any combination thereof. A manganese containing compound can be any compound or composition having manganese that produces manganese ions ($Mn^{2+}$). For example, when the manganese containing compound is administered to a subject, the manganese containing compound can produce manganese ions in vivo. Examples of manganese containing compounds include, but are not limited to, manganese chloride ($MnCl_2$), manganese dipyridoxyl diphosphate (MnDPDP), EVP 1001 (manganese gluconate/calcium gluconate 1:X manufactured by Eagle Vision and as described in detail in U.S. Pat. No. 5,980,863), TESLASCAN®, which is manafodipir trisodium, or any contrast agents which can release free manganese ions ($Mn^{2+}$). Manganese containing compounds may be used as contrast agents for imaging, such as imaging with an MRI (magnetic resonance imaging), because of the unique property of the constituent manganese ions to act as an intracellular contrast agent. Generally, contrast agents are a group of contrast media that are used to improve visibility of internal cellular structure and to improve visibility of internal body structures such as tissues within a subject. In one aspect, the manganese containing compound is manganese chloride or manganese dipyridoxyl diphosphate, which can dissociate in vivo into manganese ions and chloride or manganese ions and dipyridoxyl diphosphate, respectively. As stated herein, manganese ions can be taken up by the cell, and due to manganese ion's properties, act in manner similar to intracellular calcium ions while also acting as a suitable contrast agent. In one aspect, $Mn^{2+}$ uptake can occur in heart tissue and is mediated by voltage gated calcium channels such as, for example, the sodium-calcium exchanger.

The manganese containing compound can be formulated with a variety of pharmaceutically-acceptable carriers known to those skilled in the art. Examples of standard carriers for administration to humans include solutions such as sterile water, saline, and buffered solutions at physiological pH. In one aspect, the manganese containing compound can be administered to a subject via injection (e.g., intravenously, subcutaneously, and intramuscularly). Preparations for administration via injection include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. In certain aspects, a standard protocol, for example, the American College of Radiology's "Practice Guideline for the Use of Intravascular Contrast Media" (Revised 2007, Res. 39, Effective Oct. 1, 2007) may be followed for the administration of the contrast agents described herein.

It will be appreciated that the actual preferred amounts of manganese containing compound administered to the subject can vary according to the particular compositions formulated, the mode of application, and the particular situs and mammal being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999)).

Optionally at step 14, the practitioner can administer an inhibitor of the sodium-calcium exchanger (commonly referred to an "NCX inhibitor"). In one aspect, the NCX inhibitor is administered at some time after the manganese containing compound or manganese ions are administered. In this aspect, the NCX inhibitor administered can be administered 30 to 60 minutes post-$Mn^{2+}$ or post manganese containing compound infusion. Examples of suitable NCX inhibitors include, but are not limited to, SEA 0400, KB-R7943, and SN-6, administered alone or in combination. The sodium-calcium exchanger (NCX) is an antiporter membrane protein which removes calcium from cells. Since this transport is electrogenic, depolarization of a cell's membrane can reverse the exchanger's direction. When depolarized, the sodium-calcium exchanger functions in reverse mode and this causes intracellular $Ca^{2+}$ concentration overload, which can lead to cellular and tissue death. Thus, when indirectly measuring $Ca^{2+}$ efflux according to the method 10 of the present invention, it may be advantageous to utilize a NCX inhibitor to limit the number of variable cellular conditions.

Once administered to the subject, the manganese containing compound begins to dissociate into manganese ions ($Mn^{2+}$), which are taken up by cells (e.g., myocardiate cells and cardiate cells), and the other components of the manganese containing compound (e.g., counterion). Numerous protein transporters aid in the cellular uptake of manganese ions. For example, the sodium and calcium exchanger and various other protein pumps, transporters, and exchangers facilitate the uptake of manganese ions. The cell generally requires some time to take up the manganese ions.

At step 16, the practitioner allows sufficient time for cellular uptake of the manganese ions. In certain aspects, free $Mn^{2+}$ can take about 8 to 35 minutes to be taken up by a cell via various protein transporters such as the sodium-calcium exchanger, L-type $Ca^{2+}$ channels, and $Ca^{2+}$ related channels pumps and exchangers. In other aspects, a manganese containing compound is administered and the $Mn^{2+}$ dissociates from the remaining manganese containing compound, which can include a chelating agent, and is this taken up by a cell. Thus in this aspect, $Mn^{2+}$ uptake typically occurs between about 15 minutes to 1 hour after administration. In other aspects, cellular uptake can occur almost immediately upon $Mn^{2+}$ infusion (e.g., 0-1 minutes or 0 to a few minutes) or cellular uptake can occur (or continue to occur) about 2 hours after $Mn^{2+}$ infusion.

At step 18, the practitioner images the efflux of the manganese ions from the cells with appropriate imaging technology. In one aspect, the practitioner images the cells of interest with an MRI machine so as to measure the efflux of manganese ions. For example, the practitioner can use an MRI mapping technique, a Manganese-enhanced MRI (MEMRI) mapping technique, or a combination thereof. MEMRI may be advantageous because comprehensive quantitative information may be obtained without repositioning the subject. Preferably, magnesium ion efflux from a cell is measured in vivo, although in alternative embodiments, the magnesium ion efflux can be measured in vitro or ex vivo.

In one aspect, manganese efflux can be calculated from MEMRI. For example, temporal in vivo $\Delta R_1$ values for the left ventricular free wall are calculated from manganese-enhanced MRI (MEMRI) $T_1$ maps as (post-$MnCl_2$ infusion $1/T_1$)−(pre-$MnCl_2$ infusion $1/T_1$). The temporal $\Delta R_1$ values are then fit to a first order exponential decay using a least-square fitting technique with GraphPad Prism statistics software. Values of the exponential $\Delta R_1$ half-life are calculated from the exponential fit. To ascertain the relationship between the temporal response of $\Delta R_1$ post-$MnCl_2$ infusion and the absolute myocardial Mn concentration, cardiac samples are analyzed using ICP-MS. The temporal absolute Mn concentration data can be fit in the same way as the in vivo data with a first-order exponential. As shown in the examples section, using this protocol, there is no significant difference between the in vivo LV Wall $\Delta R_1$ half-life and the absolute cardiac Mn concentration half-life obtained via elemental analysis (p=0.64). Therefore, manganese efflux half-life can be calculated by fitting a first order exponential to the temporal $\Delta R_1$ data.

At step 18, the practitioner correlates the efflux of the manganese ions from the cell with the efflux of calcium ions from the cell. In one aspect, $Mn^{2+}$ efflux can reflect actual myocardial $Ca^{2+}$ efflux. As described above, manganese ions have similar chemical and physical properties compared to calcium ions. Therefore, the methods described herein provide a precise way to measure manganese efflux from cells, which in turn can be used to predict an increase or decrease in calcium efflux.

At step 20, the practitioner creates a treatment regimen tailored to the subject based on the measured value of the efflux of the calcium ions. In this aspect, therapeutic agents may be administered in a dose dependent manner based on the amount of $Ca^{2+}$ from the cells. Therapeutic agents may include, for example, any therapeutic agent that affects $Ca^{2+}$ flux dynamics or fluctuations such as angiotensin converting enzyme (ACE) inhibitors, $Ca^{2+}$ channel blockers, NCX inhibitors, and any $Ca^{2+}$ flux modulating compounds/therapeutics. In certain aspects, this tailored treatment regimen may be further monitored by the methods described herein, by routine clinical laboratory tests, and by other techniques known in the art. Based on these results, a subject's treatment regimen (i.e. dosing schedule and amounts) may be further tailored to meet that individual's needs or discontinued.

Figure 6:
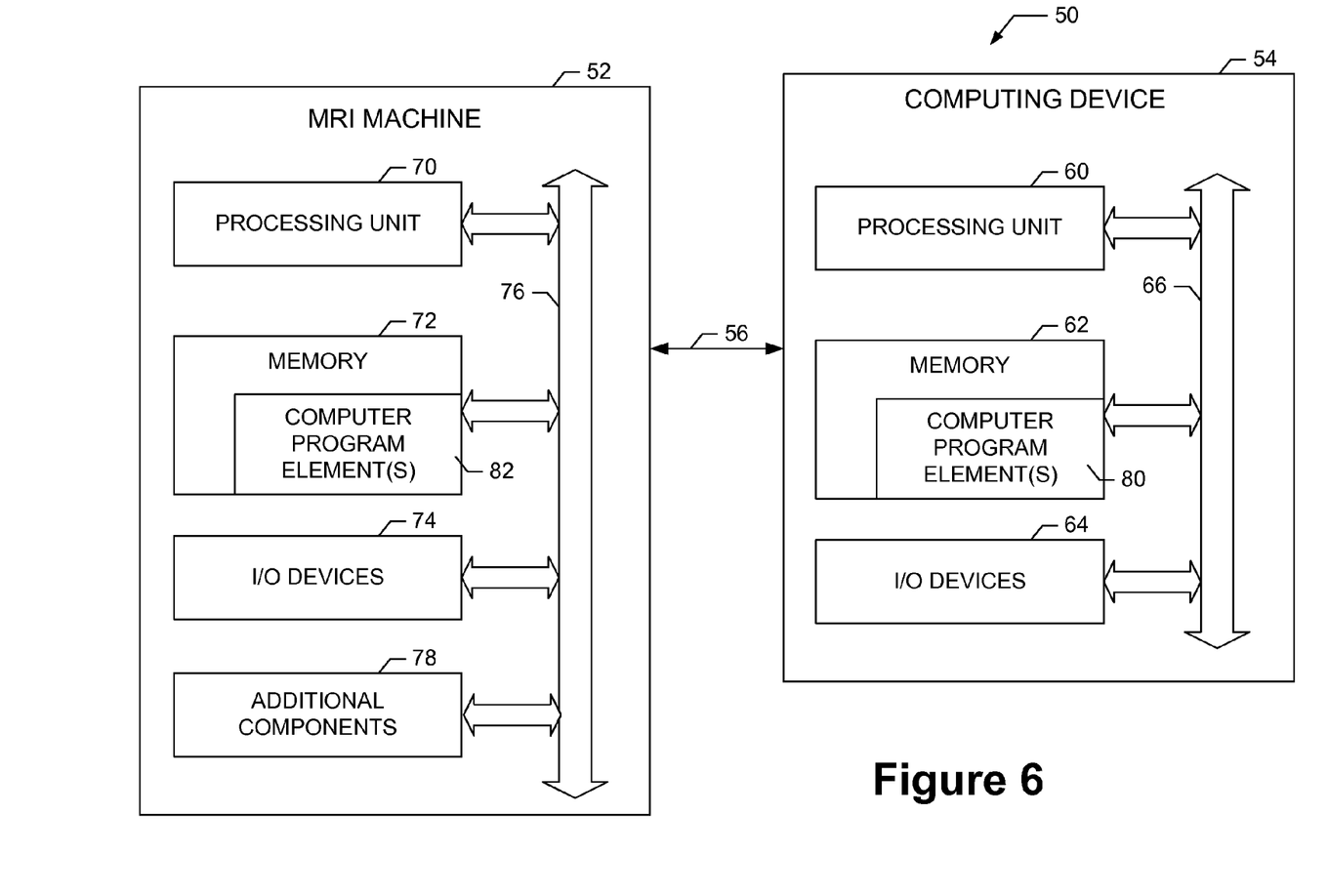
FIG. 6 depicts a block diagram of an example of a suitable computing system environment on which the invention may be implemented.

With reference to FIG. 6, an exemplary system 50 for implementing the data acquisition (i.e., imaging) and data analysis (e.g., measuring manganese ion efflux concentration) includes a conventional MRI machine 52 configured for MEMRI imaging coupled to a general-purpose computing device in the form of a computer 54. The MRI machine 52 can be operatively coupled to the computer 54 via a suitable interface 56, such as a cable or via one or more networks, including but not limited to: the Internet, a local area network (LAN), a wide area network (WAN), via a telephone line using a modem (POTS), Bluetooth, WiFi, cellular, optical, satellite, RF, Ethernet, magnetic induction, coax, RS-485, or other like networks. In such an embodiment, data obtained from scans by the MRI device 52 can be transmitted to the computer 54 for further manipulation.

Components of computer 54 may include, but are not limited to, a processing unit 60, a system memory 62, i/o devices 64, and a system bus 66 that couples various system components including the system memory to the processing unit. All of the components of the computer 54 are conventional and well known to those skilled in the art.

For example, the processing unit 60 is a hardware device for executing software that can be stored in memory 62. The processing unit 60 can be virtually any custom made or commercially available processor, a central processing unit (CPU), data signal processor (DSP) or an auxiliary processor among several processors associated with a server, and a semiconductor based microprocessor (in the form of a microchip) or a macroprocessor. Examples of suitable commercially available microprocessors are as follows: an 80×86 or Pentium series microprocessor from Intel Corporation, U.S.A., a PowerPC microprocessor from IBM, U.S.A., a Sparc microprocessor from Sun Microsystems, Inc, a PA-RISC series microprocessor from Hewlett-Packard Company, U.S.A., or a 68xxx series microprocessor from Motorola Corporation, U.S.A.

The memory 62 can include any one or combination of volatile memory elements (e.g., random access memory (RAM, such as dynamic random access memory (DRAM), static random access memory (SRAM), etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 62 may incorporate electronic, magnetic, optical, and/or other types of storage media. Note that the memory 62 can have a distributed architecture, where various components are situated remote from one another, but can be accessed by the processing unit 60.

Input/output devices 64 can include one or more of the following: a keyboard, a microphone, a pointing device, such as a mouse, trackball or touch pad, a joystick, game pad, satellite dish, scanner, monitor, display device, speaker, printer, or the like.

The system bus 66 can be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Additionally or alternatively, the methods of the present invention can be implemented in a conventional MRI machine having computing components similar to the computer 54, including a processing unit 70, a system memory 72, i/o devices 74, and a system bus 76 that couples various system components including the system memory to the processing unit 60, in addition to the conventional MRI components 78 (such as a coil, magnets, etc.). MRI machines are well known in the art, and thus, the internal components will not be discussed in detail.

The methods of the present invention can be embodied in computer program elements 80, 82. Computer program elements 80, 82 of the invention may be embodied in hardware (such as in the processing unit 70 or memory 72 of the MRI machine 52 or in the processing unit 60 or memory 62 of the computer 54 or computing device operatively connected to an MRI machine) and/or in software (including firmware, resident software, micro-code, etc.). If implemented in hardware, a system of the present invention be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. Computer readable media can be any available media that can be accessed by a computer or computing device and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

Experimental Protocol

MEMRI experiments were performed in 62 healthy adult male C57Bl/6 mice (6-14 weeks old, 24.0±1.9 g) following the guidelines of the Institutional Animal Care and Use Committee at the Medical College of Georgia, Augusta, Ga., USA. For all experimental procedures, the animals were anesthetized with a mixture of medical air, oxygen (1:1) and 2.5-3.0% isoflurane. The heart rate (HR) was maintained at 436±42 beats per minute (bpm) throughout the experiment by carefully adjusting the level of isoflurane. A custom-made water bed set at 38° C. maintained a constant animal body temperature in the cradle throughout the MEMRI procedure.

The mice were randomized into three experimental groups: single $MnCl_2$ dose to establish baseline for comparison (control; n=14 mice), low dose SEA0400 (n=8 mice), and high dose SEA0400 (n=7 mice). After the proper level of anesthesia was achieved in each animal, $MnCl_2$ infusions (prepared from a 60 mM stock solution) were administered intravenously via the tail vein. All $MnCl_2$ infusions were completed at a constant rate of 0.6 ml/hr with the aid of a syringe pump (KD Scientific Inc., Holliston, Mass., USA), with an average infusion time of 7.6±0.5 minutes. For the control group, a single $MnCl_2$ dose of 190±2 nmoles/g total body weight (BW) was infused in the mice. This $MnCl_2$ dose was previously shown not to cause cardiotoxic effects, and was found to lie at the high dose end of the linear $Mn^{2+}$ uptake regime. $T_1$-maps were acquired for a sample of mice (n=33) prior to $MnCl_2$ infusion for obtaining the baseline (pre-$MnCl_2$ infusion) $R_1$ values required for calculation of $\Delta R_1$. Then $T_1$-maps were acquired for the control mice at various time points post-$MnCl_2$ infusion, ranging from 0.2 hrs to 12 hours. The maps were not acquired during the first 0.2 hours following $MnCl_2$ infusion so as to allow for assumed blood pool clearance.

Once the initial control experiments were performed, the NCX inhibitor SEA0400 was used to assess the $Mn^{2+}$ efflux mechanism in vivo. As with the control mice, 190±2 nmoles/g of $MnCl_2$ was administered to each SEA0400 group mouse while on a surgical bench so as to minimize the required time in the MRI magnet. One hour following the $MnCl_2$ infusion, the SEA0400 mice were injected intraperitoneally with either a low dose (20±0.2 mg/kg) or a high dose (50±0.2 mg/kg) of SEA0400 (Taisho Pharmaceutical Co. Ltd, Tokyo, Japan) prepared in a lipid emulsion vehicle consisting of 20% soybean oil. This time period of one hour post-infusion was used because the $Mn^{2+}$ uptake in myocardial tissue was assumed to have reached a steady state following blood pool washout. MEMRI $T_1$-maps for both SEA0400 groups were acquired at various time points beginning 1.3 hours after the MnCl$_2$ infusion until 14.2 and 10.6 hours post-MnCl$_2$ infusion for the low and high SEA0400 dose groups, respectively.

As previously stated, all mice were anesthetized during the experimental procedures: contrast agent infusion, drug administration, and imaging sessions. The mice were allowed to recover between procedures so as to maximize the time each mouse was under anesthesia to 2.5 hours, which was then followed by a recovery period of at least 2.5 hours. This protocol minimized any physiological effects caused by the anesthesia; imaging time points selected for each mouse followed these guidelines. In addition, efforts were made to alter the time interval between successive data points so as not to bias the results with potential anesthesia effects. The $\Delta R_1$ washout curves were produced for each group by calculating $T_1$ values in the left ventricular free wall from $T_1$-maps acquired at the various time point post-MnCl$_2$ infusion. A subgroup of randomly selected animals (n=16) was sacrificed immediately after imaging to measure absolute Mn content in heart tissue (n=14) and blood samples (n=6) by inductively coupled plasma-mass spectrometry (ICP-MS) analysis (CANTEST Ltd., North Vancouver, BC, Canada). The samples were harvested approximately one hour after the initiation of the final $T_1$-map. This time delay was due to the length of time required to acquire the $T_1$-map, and the time required to harvest the samples, and remained constant for all of the samples.

Figure 2A:
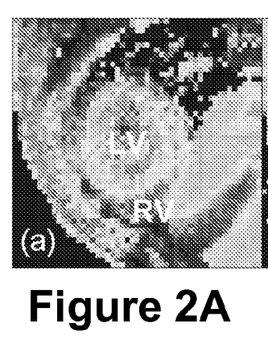
FIGS. 2A through 2C show sample cardiac short axis $T_1$-maps pre-$MnCl_2$ and post-$MnCl_2$ infusion.
Figures 2B, 2C:
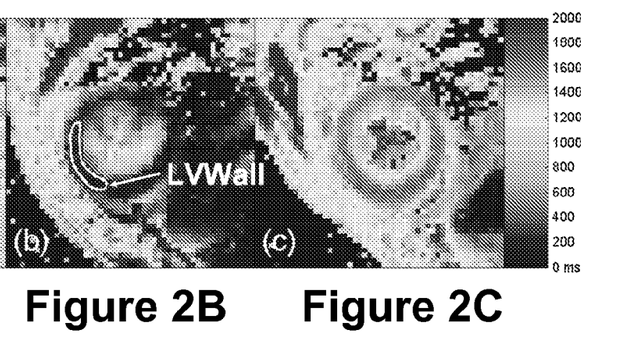

FIG. 2 shows sample cardiac short axis $T_1$-maps pre-MnCl$_2$ infusion (FIG. 2A), 0.2 hours (FIG. 2B), and 5 hours (FIG. 2C) post-MnCl$_2$ infusion. The average LV Wall ROI size was 22±5 voxels (FIG. 2B).

Figure 3A:
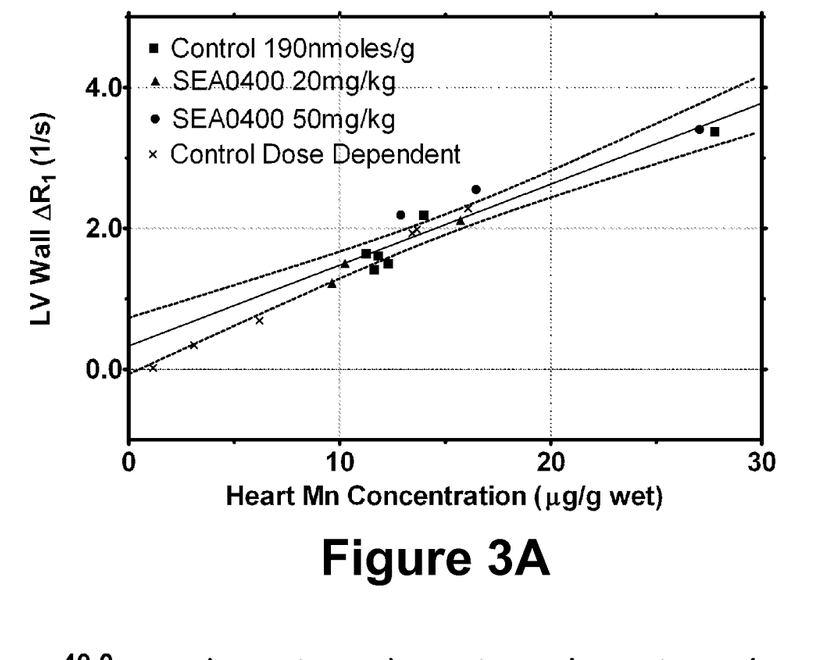
FIGS. 3A and 3B show elemental analysis data displaying the effect of the absolute heart Mn concentration on the in vivo LV Wall $\Delta R_1$ for three experimental groups.

Absolute Mn content was measured from the heart tissue and blood samples of randomly selected mice to establish the relationship between temporal changes in the LV Wall $\Delta R_1$ and absolute cardiac Mn content. FIG. 3 shows the elemental analysis results for the heart tissue samples obtained from each experimental group, with FIG. 3A showing the relationship between the LV Wall $\Delta R_1$ and absolute heart Mn concentration. No statistically significant differences between the groups were found following linear least-square fitting to the data. However, a common fit with a gradient of 0.10 (p=0.38) and y-intercept of 0.48 (p=0.08) was found. The finding of no statistically significant difference in the slopes of the $\Delta R_1$/Mn concentration curves between the control and SEA0400 groups suggests that myocardial relaxivities were not influenced by administration of SEA0400. A linear fit to all of the data groups was demonstrated with the 95% confidence band in FIG. 3A. This corresponding myocardial relativity was 6.92 mM$^{-1}$s$^{-1}$ using an assumed myocardial tissue density of 1.055 g/ml.

Figure 3B:
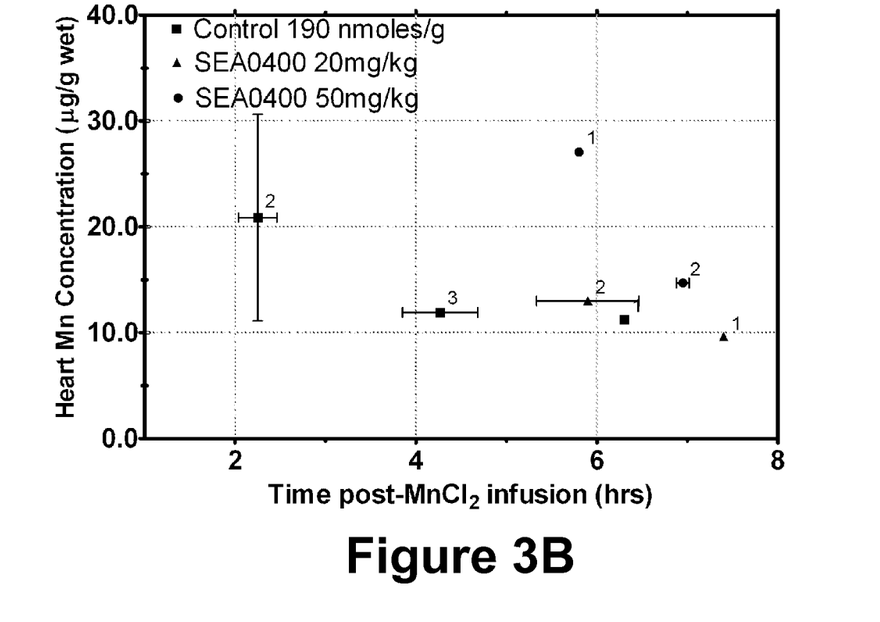

FIG. 3B shows the temporal response of the absolute cardiac Mn concentration. The Mn concentration for the control group was reduced from an average of 20.9±9.7 µg/g at the 2 hour time point to approximately 11.9±0.3 µg/g 4 hours post-MnCl$_2$ infusion. At approximately 6 hours post-MnCl$_2$, the 50 mg/kg SEA0400 group exhibited a Mn concentration of 27.1 µg/g, which was more that twice the concentration of the control group at the same time point.

$T_1$-maps were acquired from blood samples taken from 16 mice (n=3 pre-MnCl$_2$, n=6 for the control, n=4 for the SEA0400 20 mg/kg and n=3 for the SEA0400 50 mg/kg group). $\Delta R_{1,blood}$ values were calculated by subtracting the average baseline (pre-MnCl$_2$) $R_1$ value ($R_{1,blood,baseline}$=1.28±0.17/sec), from the individual $R_1$ values post-MnCl$_2$ infusion. The average $\Delta R_{1,blood}$ for the three groups was 0.17±0.48/sec.

In addition to the in vivo $\Delta R_{1,blood}$ calculations, elemental analysis was performed on the blood samples from 6 mice (n=2 baseline; n=2 control; n=2 SEA0400 50 mg/kg). The average baseline Mn concentration was 0.09±0.01 mg/ml, with the corresponding concentrations for the control and SEA0400 groups being 0.19±0.05 (t=5±1.8 hrs post-MnCl$_2$ infusion) and 0.18±0.01 (t=7±0.1 hrs post-MnCl$_2$ infusion) mg/ml respectively. The increase in blood Mn concentration for both groups, although non-zero, is minute compared to the infusion concentration which cannot be detected as an increase in $\Delta R_{1,blood}$. When fit with a linear least-square best fit no temporal trend for the blood Mn concentration was observed (slope=0.01±0.01 mg/ml/hour, r$^2$=0.58) over the time range of sample acquisition (t=3.7-7 hours).

Figure 4:
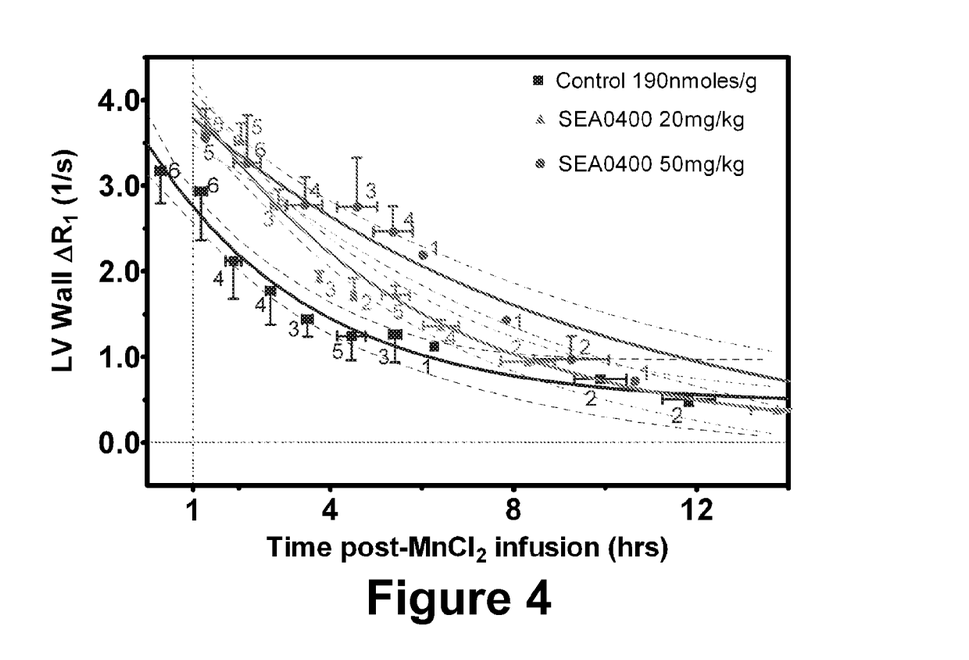
FIG. 4 shows the effect of the NCX channel inhibitor SEA0400 on the temporal changes in $\Delta R_1$, measured in the LV Wall.

Values of $\Delta R_1$ were calculated by subtracting the average baseline ROI $R_1$ ($R_{1,baseline,LVWall}$=0.78±0.04/sec from 33 mice) from the post-MnCl$_2$ infusion ROI $R_1$ value. Infusion of 190 nmoles/g BW MnCl$_2$ solution into the control group produced a LV Wall $\Delta R_1$ washout curve as shown in FIG. 4 (squares). Fitting a least-square first order exponential to the individual data points (r$^2$=0.83) gave $\Delta R_{1,0}$=3.4±0.3/sec. The $T_1$ shortening effect was rapidly attenuated, with a $\Delta R_1$ half-life of 3.4±0.6 hours (n=14, total number of $T_1$-maps=36).

The effect of the NCX inhibitor SEA0400 on the temporal changes in LV Wall $\Delta R_1$ are also shown in FIG. 4. These washout curves were obtained following a single intraperitoneal injection of either 20 mg/kg or 50 mg/kg SEA0400 one hour post-MnCl$_2$ infusion. Least-square first order exponential curves were fit to the temporal LV Wall $\Delta R_1$ data, beginning at one hour post-MnCl$_2$ infusion (t=1 hour). For the 50 mg/kg SEA0400 group (circles) (n=7, total number of $T_1$-maps=29), the exponential curve was extended, with a $\Delta R_1$ reduction half-life of 5.6±1.1 hrs and a $\Delta R_{1,0}$=4.3±0.4/sec (r$^2$=0.87). The 20 mg/kg SEA0400 group (triangles) displayed a half-life of 3.6±0.5 hrs and a $\Delta R_{1,0}$=4.8±0.2/sec (n=8, total number of $T_1$-maps=33, r=0.91). For comparison, the control group was also fit to a least-square first order exponential curve excluding data for t<1 hour. This fit yielded a half-life of 3.2±0.5 hrs and a $\Delta R_{1,0}$=3.5±0.8/sec (r$^2$=0.77). All three washout curves in FIG. 4 include the 95% CI envelopes, where regions with no overlap between groups demonstrate significance at that particular time.

In the time range of 4.9-5.9 hours post-MnCl$_2$ infusion, the average $\Delta R_1$ values for the SEA0400 groups were 2.46±0.29/sec (n=4) and 1.72±0.24/sec (n=5) for 50 mg/kg and 20 mg/kg doses respectively, as compared to the control group of 1.27±0.28/sec (n=4). This range was selected whereby sufficient time post-SEA0400 administration had elapsed allowing observation of any potential drug effects. An ANOVA test comparing the LV Wall $\Delta R_1$ values for the three groups within this time interval showed a significant difference in LV Wall $\Delta R_1$ between the groups (p<0.05). Further Tukey post hoc comparisons showed significant differences between all group combinations (p<0.05).

Figure 5A:
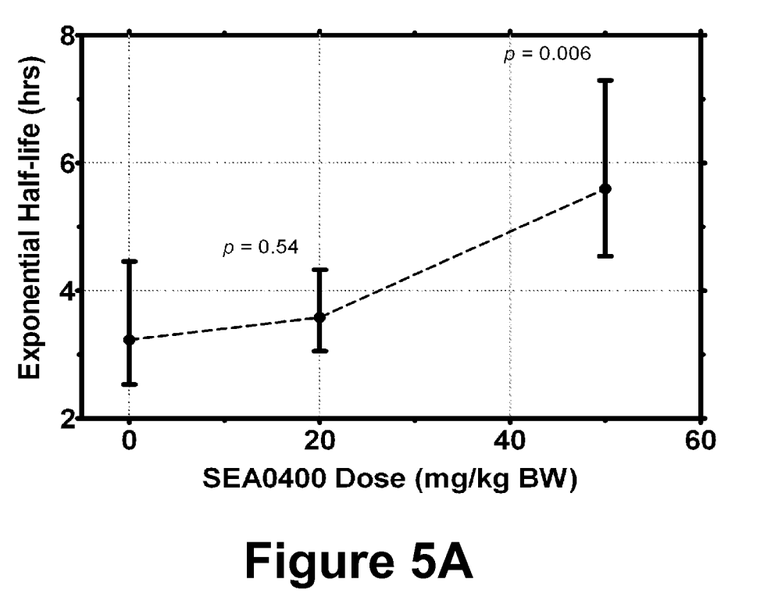
FIG. 5A shows the dose dependence of NCX inhibitor SEA0400 on temporal LV Wall $\Delta R_1$ washout half-life and FIG. 5B shows the extrapolated $\Delta R_1$ at the time of $MnCl_2$ infusion ($\Delta R_{1,0}$).
Figure 5B:
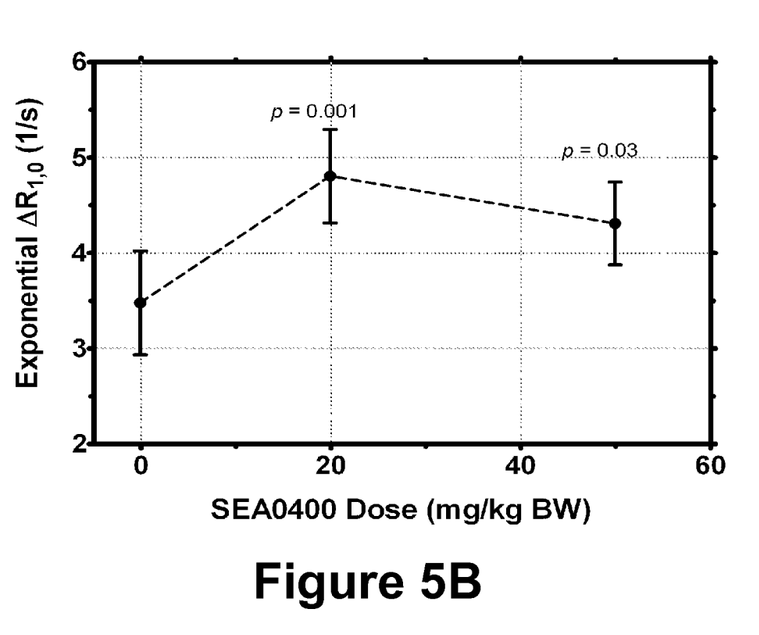

FIG. 5 illustrates the dose dependence of SEA0400 on the exponential temporal response of the LV Wall $\Delta R_1$ washout curves. FIG. 5A shows the dose dependence on half-life; FIG. 5B shows the dependence on $\Delta R_{1,0}$. For both curves, SEA0400 dose was plotted against the relevant exponential fit parameters of the washout data (t≥1 hour) with the 95% CI shown. An extra sum-of-squares F test showed that the washout half-life was significantly different between these three groups (p=0.002). The 50 mg/kg group had a half-life significantly different from the control group (p=0.006), although the half-life for the 20 mg/kg group was not statistically different from the control group (p=0.54). No statistical difference was found between $\Delta R_{1,0}$ measured in the two SEA0400 groups (p=0.12), although a statistical difference existed between $\Delta R_{1,0}$ when comparing all three groups (p=0.004). These findings suggest that SEA0400 caused an initial increase in $\Delta R_1$ that was independent of dose, but a higher dose of SEA0400 was required to reduce the rate of $\Delta R_1$ reduction.

The average post-MnCl$_2$ infusion HR for the control group was 456±30 bpm with the SEA0400 groups having heart rates of 449±30 bpm and 443±28 bpm for the 20 mg/kg and 50 mg/kg groups, respectively. No significant differences in HR was found between the experimental groups (p=0.08).

Manganese-Enhanced MRI

MEMRI data were acquired on a 7.0-T 20-cm horizontal bore Bruker BioSpec MRI spectrometer (Bruker Instruments, Billerica, Mass., USA) equipped with a micro-imaging gradient insert (950 mT/m). Animal setup procedures followed those previously described. A standard Bruker volume coil (35 mm inner diameter) was used to transmit and receive at $^1H$ frequency (300 MHz). Electrocardiographic (ECG) and respiratory signals were monitored by a physiological monitoring system (SA Instruments, INC., Stony Brook, N.Y.) with the ECG signal used to gate the images. All images were gated from the ECG R-wave acquired during end-diastole. Short axis images were acquired midway through the left ventricle and perpendicular to the long axis of the heart. A $T_1$-weighted MRI Gradient Echo Flow Compensation (GEFC) pulse sequence was used for slice localization with the imaging parameters as follows: matrix=128×128; TE=3.5 ms; TR=35 ms; slice thickness=1.0 mm; FOV=3.0×3.0 cm; flip angle=60° and NA=6. TR was purposely set at a time shorter than the R-R period (138±1.5 ms) detected on the ECG. Therefore, the true repetition time for the imaging sequence was the R-R period.

Both pre- and post-MnCl$_2$ infusion $T_1$-maps were acquired with an ECG-gated, flow-compensated Look-Locker MRI pulse sequence as previously described, with the following parameters: matrix=128×128; TE/TR=2.5 ms/10 sec; slice thickness=1.0 mm; FOV=3.0×3.0 cm; NA=2; inversion time=9 ms; average echo interval=138 ms (determined by the average R-R period before acquisition); number of echo images=50; average flip angle=11±1°. The echo interval was set as the approximate mean R-R period observed prior to the execution of each $T_1$-map sequence. The initial inversion pulse per repetition was gated with the subsequent echo pulses separated by the constant echo interval. The $T_1$ value estimation was therefore not affected by R-R period fluctuations occurring during TR. The total imaging time per $T_1$-map was approximately 43 minutes.

Data Analysis $T_1$-Mapping

The $T_1$ value of each pixel was calculated using a custom-written C$^{++}$ program. Improved neuronal tract tracing using manganese enhanced magnetic resonance imaging with fast T(1) mapping. The signal recovery of each pixel was fit from the 50 echo images by the three-parameter Levenburg-Marquardt non-linear curve-fitting algorithm. Region-of-interest (ROI) analysis was performed on the 2D $T_1$-maps using AMIDE to calculate the average regional $T_1$ value. ROIs were selected within the left ventricular free wall (LV Wall) area. In vivo $\Delta R_1$ values were calculated as (post-MnCl$_2$ infusion $1/T_1$)–(pre-MnCl$_2$ infusion $1/T_1$). The $\Delta R_1$ values were stated as a mean±standard deviation in units of [1/sec].

Statistics

Individual $\Delta R_1$ values for the control, 20 mg/kg, and 50 mg/kg SEA0400 experimental groups were fit with a least-square first order exponential decay using GraphPad Prism statistics software (GraphPad, San Diego, Calif., USA). The 95% confidence intervals (CI) for the extrapolated $\Delta R_1$ at the time of infusion, t=0, ($\Delta R_{1,0}$) and half-life values were calculated from the exponential fit. The $\Delta R_{1,0}$ and half-life values were compared between groups using an extra sum-of-squares F test, comparing the ratio of the difference between the least-square fit from the washout curves to the residual sum of squares within each curve. Comparisons between the three experimental groups were assessed using ANOVA with a Tukey post hoc test to determine differences between subgroups. The level of significance was set at $\alpha$=0.05.

Discussion

The $T_1$-mapping technique demonstrated the sensitivity of the methods described herein to detect temporal changes in relaxation rates in the LV Wall following infusion of MnCl$_2$ in healthy mice. A linear correlation between in vivo $\Delta R_1$ and the absolute cardiac Mn concentration suggested that the observed $\Delta R_1$ changes reflect changes in Mn$^{2+}$ concentration, making this technique appropriate for evaluating Mn$^{2+}$ efflux in vivo. In addition, NCX inhibition with SEA0400 extended the $\Delta R_1$ washout curve due to an assumed modulation of the Mn$^{2+}$ efflux. Therefore, this modulation of Mn$^{2+}$ following treatment with a known of NCX inhibitor, in conjunction with the establishment of Mn$^{2+}$ acting as a Ca$^{2+}$ analogue during influx, indicates that changes in Mn$^{2+}$ efflux may reflect changes in Ca$^{2+}$ efflux.

It was demonstrated that cardiac MEMRI $T_1$-mapping in mice provided a non-invasive technique to monitor changes in $\Delta R_1$ from which Mn$^{2+}$ efflux could be inferred. The temporal change in LV Wall $\Delta R_1$ after a 190 nmoles/g BW MnCl$_2$ infusion followed an exponential decay permitted inferred determinations of Mn$^{2+}$ efflux half-lives. The half-life for the control curve was 3.4 hours. The relatively fast blood pool clearance compared to the cardiac Mn$^{2+}$ clearance suggested that during the imaging time course a negligible Mn$^{2+}$ influx exists allowing for Mn$^{2+}$ efflux to be approximated with first order exponential curves. This first order exponential fit has a few potential drawbacks. If Mn$^{2+}$ efflux is multi-compartmental and occurs via multiple mechanisms, a more complicated washout form would be warranted with multiple exponential parameters. Also, the 50 mg/kg SEA0400 curve in FIG. 4 suggests that a gradual de-inhibition of the NCX occurs over time. At approximately 6 hours post-MnCl$_2$ infusion, the temporal rate of change of $\Delta R_1$ appears to increase suggesting a reduction in the inhibitory effects of the NCX inhibitor. Thus, a first order exponential fit provided a relatively good approximation for detecting Mn$^{2+}$ efflux rates and modulations.

Elemental analysis of heart tissue samples collected over the first 8 hours post-MnCl$_2$ infusion demonstrated that the reduction in LV Wall $\Delta R_1$ was linearly proportional to the myocardial Mn concentration (FIG. 3A). Also displayed in FIG. 3A is dose dependent elemental analysis data. For samples acquired approximately one hour post-infusion of 25 to 130 nmoles/g BW MnCl$_2$. The linearity of the temporal data, along with the close correlation between the two independent studies, suggested that the observed temporal changes in $\Delta R_1$ are linearly proportional to changes in Mn concentration and that Mn$^{2+}$ efflux can be estimated from the $\Delta R_1$ washout curves. If significant changes in the amount of Mn$^{2+}$ compartmentalization occurred during the experimental timeframe then the observed Mn$^{2+}$ $T_1$ relativity would not be constant as intracellular and extracellular Mn$^{2+}$ have different relaxivities. Plus, the $T_1$ relaxivity of intracellular Mn$^{2+}$ would be expected to be much higher due to protein binding. However, the finding of a linear correlation (FIG. 3A) between in vivo $\Delta R_1$ and absolute heart Mn concentration over several hours suggests that the $T_1$ relaxivity does not change over time. Therefore, the degree of compartmentalization had a relatively small contribution to $Mn^{2+}$ fluxes compared to the effect of the NCX efflux mechanism during the current experimental protocol. Furthermore, the finding of no change in relativity between the three experimental groups suggests that inhibition of the NCX with SEA0400 does not exhibit significant alterations in the amount of compartmentalization. Thus, observed changes in $\Delta R_1$ over with time may be used to quantify changes in $Mn^{2+}$ concentration in vivo under control conditions and/or when modulating NCX kinetics with the NCX inhibitor SEA0400.

Following administration of SEA0400, an increase in $\Delta R_1$ relative to the control group and independent of the SEA0400 dose was observed. One potential concern with using SEA0400 as a NCX inhibitor was the potential positive inotropic effect on rats despite having no influence on the contractility of the rabbit heart. Thus, any potential inotropic effects must first be identified as increases in cardiac contractility increase the rate of myocardial $Mn^{2+}$ influx. However, for the SEA0400 doses used in this experiment there was no significant difference found between the injection of SEA0400 and the HR. One potential explanation for the increase in $\Delta R_{1,0}$ can be made by looking at the blood sample data. A small, but non-zero, increase in blood Mn concentration was observed above the baseline level between 3.7 and 7 hours post-$MnCl_2$ infusion. Therefore, the blood Mn concentration was non-zero at the time of SEA0400 administration, one hour post-$MnCl_2$ infusion. If the rate of $Mn^{2+}$ efflux was decreased by inhibiting the NCX with SEA0400, the steady-state was disrupted and a net influx of $Mn^{2+}$ occurred via the L-type $Ca^{2+}$ channels increasing the intracellular $Mn^{2+}$ concentration and thereby explaining the $\Delta R_{1,0}$ increase.

$Mn^{2+}$ efflux could be modulated by inhibiting the NCX with SEA0400. Treating mice with 50 mg/kg SEA0400 extended the $\Delta R_1$ half-life from 3.4 to 5.6 hours. Several hours after inhibition of the NCX with 50 mg/kg SEA0400, the absolute cardiac Mn concentration was greater in the treatment group mice than the control mice (FIG. 3B). These results suggest that a greater retention of $Mn^{2+}$ occurred following $MnCl_2$ infusion. This effect was also observed with in vivo $T_1$-mapping (FIG. 4). Therefore, SEA0400 reduced the rate of $Mn^{2+}$ efflux by reducing the rate of $Mn^{2+}$ efflux via the NCX, which provided evidence that the temporal $\Delta R_1$ response reflected cardiac $Mn^{2+}$ content. Furthermore, by comparing absolute Mn concentration to the in vivo data, this study demonstrated: (1) the ability to quantify the efflux of $Mn^{2+}$ from the myocardium; (2) the capability to monitor the rate of $Mn^{2+}$ efflux; and (3) the sensitivity to examine modulation of $Mn^{2+}$ efflux following inhibition of the NCX with SEA0400. These findings, along with the biochemical similarities between $Ca^{2+}$ and $Mn^{2+}$, suggest that changes in $Mn^{2+}$ efflux may reflect fluctuations in $Ca^{2+}$ efflux and that the MEMRI $T_1$ mapping technique could be useful for monitoring disease progression.

While the invention has been described with reference to preferred and example embodiments, it will be understood by those skilled in the art that a variety of modifications, additions and deletions are within the scope of the invention, as defined by the following claims.

What is claimed is:

1. A method of measuring calcium ion efflux from cells comprising:
   a. obtaining one or more baseline $T_1$-map(s) of the cells prior to contacting the cells with a plurality of manganese ions;
   b. contacting the cells with a plurality of manganese ions;
   c. obtaining one or more post-$Mn^{2+}$ $T_1$ map(s) of the cells after contacting the cells with a plurality of manganese ions;
   d. measuring the efflux of the manganese ions from the cells comprising measuring temporal $\Delta R_1$ values and fitting the values to an exponential decay plot, wherein each $\Delta R_1$ is calculated by the formula;

$\Delta R_1 = (1/\text{post-}Mn^{2+}T_1 \text{ map}) - (1/\text{baseline } T_1 \text{ map})$ and
   e. correlating efflux of the manganese ions from the cells with the relative efflux of calcium ions from the cells.

2. The method of claim 1, wherein the cells comprises a cardiomyocyte or a cell undergoing calcium ion efflux.

3. The method of claim 1, wherein steps (a) and (c) comprise imaging the cells with an MRI machine.

4. The method of claim 1, wherein steps (a) and (c) comprise an MRI mapping technique, a Manganese-enhanced MRI (MEMRI) mapping technique, or a combination thereof.

5. The method of claim 1, wherein step (d) comprises measuring temporal $\Delta R_1$ values and fitting the values to a first order or multiple exponential decay plot.

6. The method of claim 1, wherein the cells are contacted with a sodium-calcium exchanger inhibitor prior to step (c).

7. The method of claim 6, wherein the sodium-calcium exchanger inhibitor comprises SEA 0400, KB-R7943, SN-6, or any combination thereof.

8. The method of claim 1, wherein the cells are contacted in vivo.

9. A method for measuring calcium ion efflux in a subject after an ischemic event, comprising:
   a. obtaining one or more baseline $T_1$-map(s) of the subject prior to administering to the subject a manganese containing compound;
   b. administering to the subject a manganese containing compound;
   c. obtaining one or more post-$Mn^{2+}$ $T_1$ map(s) of the subject after administering the manganese containing compound to the subject;
   d. measuring efflux of the manganese ions dissociated from the manganese containing compound comprising measuring temporal $\Delta R_1$ values and fitting the values to an exponential decay plot, wherein each $\Delta R_1$ is calculated by the formula;

$\Delta R_1 = (1/\text{post-}Mn^{2+}T_1 \text{ map}) - (1/\text{baseline } T_1 \text{ map})$;

and
   e. correlating efflux of the manganese ions with the relative efflux of calcium ions.

10. A method of treating a human or animal subject after an ischemic event, comprising:
   a. obtaining one or more baseline $T_1$-map(s) of the subject prior to administering to the subject a manganese containing compound;
   b. administering to the subject a manganese containing compound;
   c. obtaining one or more post-$Mn^{2+}$ $T_1$ map(s) of the subject after administering the manganese containing compound to the subject;
   d. measuring efflux of the manganese ions dissociated from the manganese containing compound comprising measuring temporal $\Delta R_1$ values and fitting the values to an exponential decay plot, wherein each $\Delta R_1$ is calculated by the formula;

$\Delta R_1 = (1/\text{post-}Mn^{2+}T_1 \text{ map}) - (1/\text{baseline } T_1 \text{ map})$;

e. correlating efflux of the manganese ions with the relative efflux of calcium ions; and f. administering an appropriate amount of a therapeutic agent to the subject based on the amount of efflux of calcium ions calculated in step (e).

11. The method of claim 10, wherein the ischemic event is a myocardial event.

12. The method of claim 11, wherein the myocardial event comprises heart palpitations, a myocardial infarction, chest pain, shortness of breath, nausea, vomiting, sweating, anxiety, fatigue, heart attack, cardiac arrest, heart failure, atrial fibrillation, or any combination thereof.

13. The method of claim 10, wherein the manganese containing compound comprises manganese chloride ($MnCl_2$), EVP 1001, manafodipir trisodium (TESLASCAN®), or any combination thereof.

14. The method of claim 10, wherein steps (a) and (c) comprise imaging the subject with an MRI machine.

15. The method of claim 10, wherein steps (a) and (c) comprise MRI mapping technique, a Manganese-enhanced MRI (MEMRI) mapping technique, or a combination thereof.

16. The method of claim 10, wherein step (d) comprises measuring temporal $\Delta R_1$ values and fitting the values to a first order or multiple exponential decay plot.

17. The method of claim 10, wherein the subject is administered a sodium-calcium exchanger inhibitor prior to step (c).

18. The method of claim 17, wherein the sodium-calcium exchanger inhibitor comprises SEA 0400, KB-R7943, SN-6, or any combination thereof.

19. The method of claim 10, wherein the therapeutic agent comprises an angiotensin converting enzyme (ACE) inhibitor, a $Ca^{2+}$ channel blocker, a sodium calcium exchanger inhibitor, or any combination thereof.

20. The method of claim 1, wherein the one or more post-$Mn^{2+}$ $T_1$ maps are obtained on or after 0.2 hours after step (b).

21. The method of claim 10, wherein the therapeutic agent comprises a $Ca^{2+}$ flux modulator.

* * * * *